United States Patent [19]

Mörsdorf et al.

[11] Patent Number: 4,600,721
[45] Date of Patent: Jul. 15, 1986

[54] PHARMACEUTICAL PREPARATION

[75] Inventors: Peter Mörsdorf, Cadolzburg; Helmut Schickaneder, Eckental; Heidrun Engler, Cadolzburg; Istvan Szelenyi, Schwaig; Kurt H. Ahrens, Nuremberg; Kay Brune, Marloffstein, all of Fed. Rep. of Germany

[73] Assignee: Ludwig Heumann & Co., GmbH, Fed. Rep. of Germany

[21] Appl. No.: 716,408

[22] Filed: Mar. 27, 1985

[30] Foreign Application Priority Data

Apr. 12, 1984 [DE] Fed. Rep. of Germany ....... 3413876

[51] Int. Cl.$^4$ .................... A61K 31/42; A61K 31/425
[52] U.S. Cl. .................................... 514/367; 514/377
[58] Field of Search ............................... 514/367, 377

[56]     References Cited
    FOREIGN PATENT DOCUMENTS

| 2250077 | 4/1973 | Fed. Rep. of Germany . |
| 2727924 | 4/1978 | Fed. Rep. of Germany . |
| 2703280 | 8/1978 | Fed. Rep. of Germany . |
| 51-35428 | 1/1976 | Japan . |

Primary Examiner—Stanley J. Friedman
Attorney, Agent, or Firm—Ostrolenk, Faber, Gerb & Soffen

[57]     ABSTRACT

Pharmaceutical preparations having an antiphlogistic action are described. The preparations contain, as active ingredient, a benzazole derivative corresponding to the general tautomeric formulae I

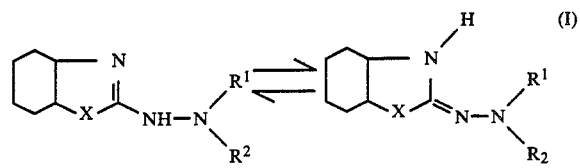

wherein X represents a sulphur or oxygen atom and $R^1$ represents a hydrogen atom and $R^2$ a hydroxymethyl, formyl, lower carbalkoxy or lower acyl group or $R^1$ and $R^2$ together represent the group

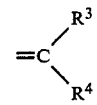

wherein $R^3$ and $R^4$ denote, independently of one another, a hydrogen atom or a $C_1$–$C_6$-alkyl group, or they contain a physiologically acceptable salt thereof. These pharmaceutical preparations are suitable in particular for the treatment of inflammatory conditions and for inhibiting the lipoxygenase and/or cyclooxygenase route of arachidonic acid metabolism.

24 Claims, No Drawings

PHARMACEUTICAL PREPARATION

DESCRIPTION

This invention relates to a pharmaceutical preparation which has a powerful antiphlogistic action. The invention further relates to the use of certain benzazole derivatives for the production of a pharmaceutical preparation with a high antiphlogistic action and to the use of these benzazole derivatives for the treatment of inflammatory conditions. Compounds corresponding to the general formula I have in part (X=S) already been described in Japanese Offenlegungsschrift No. 76 35 428 (1976). These compounds may be prepared by a chemical condensation reaction in which equimolar solutions of a 2-hydrazino-benzazole derivative is reacted with aldehydes or ketones in acetic acid at 50° C. for 4 hours. After concentration of the solution by evaporation, the benzazole derivative corresponding to the general formula I is obtained analytically pure by crystallisation. Japanese Offenlegungschrift No. 76 35 428 (1976) also describes pesticides containing benzothiazole compounds but makes no reference to any medicinal effects of the benzazole compounds described there.

The synthesis for preparing benzazole derivatives (X=S) wherein $R^1$ denotes a hydrogen atom and $R^2$ denotes a formyl group has been described in DE-OS No. 2 703 280 and DE-OS No. 2 727 924. The corresponding compounds in which $R^2$ denotes a hydroxymethyl group may readily be prepared from the aforementioned compounds by reduction with an organometallic reducing agent such as, for example, lithium alanate, in an inert solvent such as tetrahydrofuran. These benzothiazole compounds may be prepared by the following method: Equimolar solutions of 2-hydrazinobenzothiazole and formamide in acetic acid are heated to 80° C. for 5 hours. The product is purified by crystallisation.

According to the above mentioned Offenlegungsschriften, benzothiazole derivatives are also used for carrying out vinyl chloride polymerisation, but the said documents make no reference to any medicinal actions of the benzothiazole derivatives described there.

The preparation of benzothiazole derivatives in which $R^1$ represents a hydrogen atom and $R^2$ represents an acyl group has been described in DE-OS No. 2 250 077. The said document also mentions pesticides containing benzazole derivatives but does not describe any medicinal actions of these compounds. Corresponding compounds in which X is an oxygen atom may be obtained in analogous manner.

The preparation of benzazole derivatives in which X is a sulphur or oxygen atom, $R^1$ a hydrogen atom and $R^2$ a carbalkoxy group is carried out by the reaction of 2-chlorobenzazole derivatives with hydrazinocarboxylic acid alkyl esters in ethanol at reflux temperature for 12 hours.

This invention is based on the object of providing a new pharmaceutical preparation having an antiphlogistic action.

It is now known that arachidonic acid metabolites such as cyclic endoperoxides, slow reacting substances of anaphylaxis (SRS-A, leucotrienes), prostaglandins and thromboxanes take part in the genesis of inflammatory and allergic processes. These metabolites are formed by the enzymes lipoxygenase and cyclooxygenase. It is therefore advantageous to develop medicaments containing active ingredients which develop a wider antiphlogistic action than those hitherto known. Relatively few compounds are known to date which either have a selective inhibitory action on lipoxygenase or inhibit both lipoxygenase and cyclooxygenase. Examples of known inhibitors of this kind are: Benoxaprofene and 3-amino-1-(3-trifluoromethylphenyl)-pyrazoline.

It is surprisingly found that the benzazole derivatives which may be used according to the invention have a very powerful inhibitory action which in some cases is selective for the enzyme lipoxygenase whereas other benzazole derivatives inhibit both enzymes, lipoxygenase and cyclooxygenase. The cyclooxygenase and/or lipoxygenase inhibiting benzazole derivatives according to this invention may therefore be used as medicaments for the treatment of inflammatory and allergic conditions. For example, they may be used for the prophylaxis or treatment of arthritic conditions, dermatites, inflammatory conditions of the eye, tissue necroses, tissue rejections after the performance of surgical transplants, pain, fever and asthma.

This invention therefore relates to a pharmaceutical preparation having an antiphlogistic, in particular a cyclooxygenase and/or lipoxygenase inhibitory action, characterised in that in addition to the usual auxiliary agents and vehicles it contains, as active ingredient, a benzazole derivative corresponding to the general tautomeric formulae I

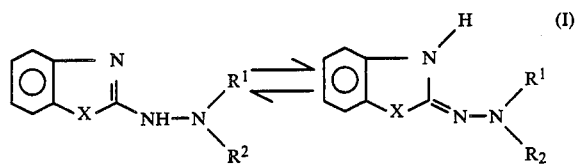

wherein X represents a sulphur or oxygen atom and $R^1$ represents a hydrogen atom and $R^2$ a hydroxymethyl, formyl, lower carbalkoxy or lower acyl group of $R^1$ and $R^2$ together represent the group

wherein $R^3$ and $R^4$ denote, independently of one another, a hydrogen atom or a $C_1$–$C_6$-alkyl group, or it contains a physiologically acceptable salt thereof. The invention further relates to the use of these derivatives and their salts for the treatment of inflammatory diseases and for the production of pharmaceutical preparations having an antiphlogistic, in particular a cyclooxygenase and/or lipoxygenase inhibitory action.

In the general tautomeric formulae I, X represents a sulphur or oxygen atom. The substituents $R^1$ and $R^2$ represent, independently of one another, a hydrogen atom or a hydroxymethyl, formyl, lower carbalkoxy or lower acyl group. The terms "lower alkoxy" and "lower acyl" are used to denote a group having 1 to 6, preferably 1 to 3 carbon atoms in the alkyl moiety. Examples of lower alkoxy groups are: methoxy, ethoxy, n-propoxy, i-propoxy, n-butoxy and t-butoxy groups, while the acetyl group and propionyl group are examples of lower acyl groups.

Compounds in which $R^1$ is a hydrogen atom and $R^2$ a formyl or carbethoxy group are preferred.

$R^1$ and $R^2$ may also together represent the group

wherein $R^3$ and $R^4$ denote, independently of one another, a hydrogen atom or a $C_1$-$C_6$-alkyl group, preferably a $C_1$-$C_3$-alkyl group. Examples of such alkyl groups are: methyl, ethyl, n-propyl, i-propyl, n-butyl, i-butyl, n-pentyl and n-hexyl groups. Compounds in which $R^3$ is a hydrogen atom and $R^4$ a methyl or ethyl group or in which $R^3$ and $R^4$ are both methyl groups are preferred.

The compound used according to the invention is preferably administered orally. The oral daily dose normally amounts to about 0.05 to 100 mg/kg of body weight, preferably from 0.1 to 10 mg/kg of body weight. In some cases, it may be necessary to deviate from these quantities, depending on the individual response to the active ingredient or the nature of its formulation or the time or time interval at which it is administered. Thus, for example, in some cases, it may be sufficient to use less than the minimum quantity indicated above while in other cases it may be necessary to exceed the upper limit. When relatively large quantities are given, it may be advisable to divide them into several individual doses over the day.

For oral administration, the active ingredient may be formulated, for example, in the form of capsules which are prepared by the conventional methods with pharmaceutically acceptable excipients such as, for example, binders (such as pregelatinized corn starch, polyvinyl pyrrolidone or hydroxypropyl-methylcellulose), fillers (such as lactose, microcrystalline cellulose or calcium phosphate), lubricants (such as magnesium stearate, talcum or silica), bursting agents (for example, potato starch or sodium starch glycollate) or moistening agents (e.g. sodium lauryl sulphate).

Liquid preparations for oral administration or for direct drip feeding may, for example, have the form of solutions, syrups or suspensions or they may be prepared as dry products to be reconstituted with water or some other suitable vehicle before use. Such liquid preparations may be produced by conventional methods, using pharmaceutically acceptable additives, for example dispersing agents such as sorbitol syrup, methyl cellulose or hydrogenated edible fats, emulsifying agents, e.g. lecithin or acacia, non-aqueous vehicles, e.g. almond oil, oleaginous esters or ethyl alcohol, and preservatives such as methyl- or propyl-parahydroxybenzoates or sorbic acid.

For buccal administration, the preparations may be in the form of tablets or lozenges formulated in the usual manner. The compound according to the invention may be formulated for parenteral administration by injection or for infusion. Preparations for injection may be in unit dose form, for example in ampoules, or they may be prepared in multiple dose containers with added preservative. The preparations may also be in the form of suspensions, solutions or emulsions in oleaginous or aqueous vehicles and they may contain formulating agents such as stabilizers and/or dispersing agents. Alternatively, the active ingredient may be prepared in powder form to be reconstituted before use with a suitable vehicle such as sterile, pyrogen-free water.

The following pharmacological tests of the compounds according to the invention reveal their surprising antiphlogistic action.

RAT PAW OEDEMA TEST

Method

Acute inflammatory oedema of the paws was induced in male rats (100–120 g) by subplantar injection of 0.1 ml of 2% carrageenin (dissolved in aqueous 0.9% NaCl solution). The volume of the paws was measured with a paw volume measuring instrument 1 hour and 4 hours after the carrageenin injection. The differences in paw volume between the two measurements was calculated. The test substances were suspended in 1% tylose and administered intragastrally through a stomach tube one hour after the carrageenin injection.

The controls were given vehicle alone (1% tylose). The percentage inhibition of increase in volume in the treated animals was obtained from a comparison with the untreated controls. The average inhibitory doses ($ED_{50}$) were calculated on the basis of the regression graphs.

$ED_{50}$ values

TABLE 1

| Example No. | $ED_{50}$ (mg/kg) i.g. |
| --- | --- |
| 1 | 15 |
| 2 | 10 |
| 3 | 20 |
| 4 | 10 |
| 5 | 20 |
| 6 | 10 |
| 7 | 20 |
| 8 | 14 |

LEUCOCYTE MIGRATION TEST

Method

Polyester sponges soaked in 2% carrageenin solution were implanted subcutaneously in the neck region of male rats (140–150 g) (see G. A. Higgs et al, Eur. J. Pharmacol. 66, 81 (1980), A. W. Ford-Hutchinson et al, J.Pharmacol. Methods 1, 3 (1978)). The sponges were removed after 24 hours. The leucocytes which had migrated in were washed out with a PBS solution (pH 7.4, 0.5% trypsin, 10 units/ml of heparin) for 30 minutes at 37° C. The sponges were then carefully squeezed and centrifuged (15 minutes, 500 revs/min). The leucocytes in the washing liquid were then counted. The test substances which had been taken up in 1% tylose and the vehicle (1% tylose) were administered intragastrally with a stomach tube immediately after implantation of the sponge and then after 5 hours and after 21 hours. The percentage inhibition of leucocyte migration after administration of the test substances was determined by comparison with the controls. The average inhibitory doses ($ED_{50}$) were calculated from the regression graphs.

INHIBITORY ACTION

TABLE 2

| Example No. | Dose i.g. | Inhibition of leucocyte migration (control = 0%) |
| --- | --- | --- |
| 1 | 40 mg/kg | 50% |

TABLE 2-continued

| Example No. | Dose i.g. | Inhibition of leucocyte migration (control = 0%) |
|---|---|---|
| 2 | 50 mg/kg | 34% |
| 8 | 50 mg/kg | 67% |

INHIBITION OF PGE 2- AND LTC 4-SYNTHESES AND -RELEASE

Method

The in vitro activity of the compounds according to the invention is demonstrated by known methods (see K. Brune et al, Nature 274, 262 (1978); K. Brune et al, Naunyn Schmiedeberg's Arch. Pharmacol. 315, 269 (1981); B. A. Peskar et al (1979) in: Radioimmunoassay of drugs and hormones in cardiovascular medicine, Editors A. Albertini, M. Da Prada and B. A. Peskar, Elsevier, Amsterdam).

Inhibitory action

TABLE 3

| Example No. | PGE 2 (% of controls at) | | | | LTC 4 (% of controls at) | | | |
|---|---|---|---|---|---|---|---|---|
| | $10^{-4}$ | $10^{-5}$ | $10^{-6}$ | $10^{-7}$ | $10^{-4}$ | $10^{-5}$ | $10^{-6}$ | $10^{-7}$ |
| 1 | 12 | 38 | 89 | NM | (2) | >100 | >100 | NM |
| 2 | 20 | 43 | 103 | NM | 16 | 41 | 89 | NM |
| 3 | 8 | 37 | 61 | NM | 24 | >100 | >100 | NM |
| 8 | 82 | 112 | 105 | NM | 11 | 70 | >100 | NM |

NM = not measured

The other examples manifest similar pharmacological actions

EXAMPLE 1

Preparation of N-(benzothiazol-2-yl)-acetaldehyde hydrazone

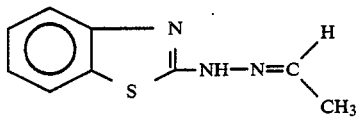

3.3 g (20 mmol) of 2-hydrazinobenzothiazole and 0.88 g (30 mmol) of acetaldehyde are dissolved in 30 ml of acetic acid (98%) and heated to 50° C. for 2 hours. After concentration of the reaction solution by evaporation, the residue is recrystallised from ethanol/isopropanol.

Colourless crystals, melting point 200°–201° C.
Yield: 2.1 g (55.3% of theoretical)
Rf=0.69 (CH$_2$Cl$_2$/MeOH 9:1)
C$_9$H$_9$N$_3$S (191): Calculated: C56.52, H 4.74, N 21.97. Found: C 56.62, H 4.76, N 21.86.

$^1$H-NMR spectrum: (d$_6$-DMSO, TMS as internal standard) δ=2.0 (d) (—CH$_3$) 3H 6.97–7.87 (m) (aromatic H̲,

5H, 11.73 (s) (N—H̲) (replaceable by D$_2$O) 1H ppm.

EXAMPLE 2

Preparation of N-(benzothiazol-2-yl)-acetone hydrazone

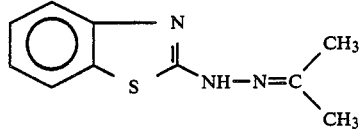

The reaction is carried out by a method analogous to that of Example 1, using 2-hydrazinobenzothiazole and acetone.

Colourless crystals, melting point 195°–197° C.
Yield: 2.3 g (56% of theoretical)
Rf=0.61 (CH$_2$Cl$_2$/MeOH 9:1)
C$_{10}$H$_{11}$N$_3$S (205): Calculated: C 58.51, H 5.40 N 20.47. Found: C 59.20, H 5.68, N 20.76.

$^1$H-NMR spectrum: (d$_6$-DMSO, TMS as internal standard) δ=1.93 (s) (2×CH$_3$) 6H, 6.83–7.70 (m) (aromatic H̲) 4H, 9.0 (s) (N—H̲) (replaceable by D$_2$O) 1H ppm.

EXAMPLE 3

Preparation of N-(benzothiazol-2-yl)-propionaldehyde hydrazone

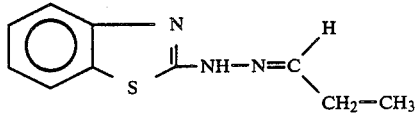

The method of preparation is analogous to that of Example 1, using 2-hydrazinobenzothiazole and propionaldehyde.

Colorless crystals, melting point 171°–172° C.
Yield: 2.6 g (63.4% of theoretical)
Rf=0.72 (CH$_2$Cl$_2$/MeOH 9:1)
C$_{10}$H$_{11}$N$_3$S (205)

$^1$H-NMR spectrum: (d$_6$-DMSO, TMS as internal standard) δ=1.07 (t) (—CH$_3$) 3H, 2.30 (m) (—CH$_2$) 2H, 6.93–7.83 (m) (aromatic H̲,

5H, 11.67 (s) (N—H̲) (replaceable by D$_2$O) 1H ppm.

EXAMPLE 4

Preparation of N-(benzothiazol-2-yl)-methyl ethyl ketone hydrazone

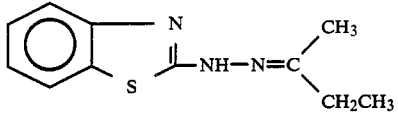

The preparation is analogous to that of Example 1, using 2-hydrazinobenzothiazole and methyl ethyl ketone.

Colourless crystals, melting point 123°–129° C.
Yield: 2.4 g (54.8% of theoretical)

Rf=0.73 (CH₂Cl₂/MeOH 9:1)

¹H-NMR spectrum: (d₆-DMSO, TMS as internal standard) δ=1.1 (t) (—CH₃) 3H, 2.0 (s) (—CH₃) 3H, 2.33 (q) (—CH₂) 2H, 6.97-7.83 (m) (aromatic H) 4H, 11.13 (s) (N—H) (replaceable by D₂O) 1H ppm.

EXAMPLE 5

Preparation of N-(benzoxazol-2-yl)-acetaldehyde hydrazone

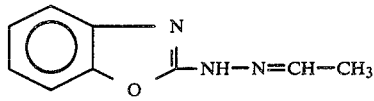

The method of preparation is analogous to that of Example 1, using 2-hydrazinobenzoxazole and acetaldehyde. Colourless crystals, melting point 169°-170° C.

Yield: 1.7 g (48.6% of theoretical)
Rf=0.75 (CH₂Cl₂/MeOH 9:1)
C₉H₉N₃O (175)

¹H-NMR spectrum: (d₆-DMSO, TMS as internal standard) δ=1.93 (d) (—CH₃) 3H, 6.93-7.67 (m) (aromatic H,

)

5H, 11.33 (s) (broad) (N—H) (replaceable by D₂O) 1H ppm.

EXAMPLE 6

Preparation of N-(benzoxazol-2-yl)-acetone hydrazone

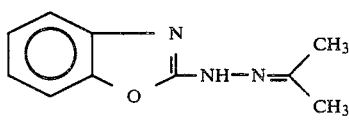

The method of preparation is analogous to that of Example 1, using 2-hydrazinobenzoxazole and acetone. Colourless crystals, melting point 157°-158° C.

Yield: 2.7 g (69.8% of theoretical)
Rf=0.74 (CH₂Cl₂/MeOH 9:1)

¹H-NMR spectrum: (d₆-DMSO, TMS as internal standard) δ=1.93 (s) (—CH₃) 3H, 2.07 (s) (—CH₃) 3H, 6.90-7.58 (m) (aromatic H) 4H, 8.67 (s) (N—H) (replaceable by D₂O) 1H ppm.

EXAMPLE 7

Preparation of N-(benzoxazol-2-yl)-propionaldehyde hydrazone

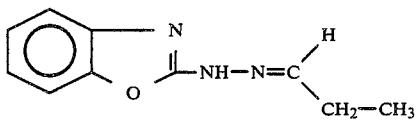

The method of preparation is analogous to that of Example 1, using 2-hydrazinobenzoxazole and propionaldehyde.

Colourless crystals, melting point 112°-113° C.
Yield: 1.9 g (50.3% of theoretical)
Rf=0.69 (CH₂Cl₂/MeOH 9:1)

¹H-NMR spectrum: (d₆-DMSO, TMS as internal standard) δ=0.95 (t) (—CH₃) 3H, 2.17 (m) (—CH₂) 2H. 6.78-7.53 (m) (aromatic H) 4H, 11.47 (s) (N—H) (replaceable by D₂O) 1H ppm.

EXAMPLE 8

Preparation of benzothiazol-2-one-(β-formyl hydrazone)

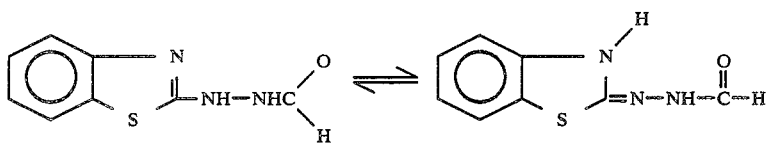

3.3 g (20 mmol) of 2-hydrazinobenzothiazole are reacted with 0.9 g (20 mmol) of formamide in 10 ml of acetic acid (98%) for 5 hours at 80° C. The residue is recrystallised from isopropanol.

Colourless crystals, melting point 226° C.
Yield: 2.0 g (52.6% of theoretical)
Rf=0.50 (CH₂Cl₂/MeOH 9:1)
C₈H₇N₃OS (193): Calculated: C 49.73, H 3.65, N 21.75. Found: C 50.35, H 3.76, N 21.63.

¹H-NMR spectrum: (d₆-DMSO, TMS as internal standard) δ=6.93-7.87 (m) (aromatic H) 4H 8.17 (s)

$(-\overset{O}{\underset{}{C}}-H)$ 1H, 10.17 (s) (2×N—H) (replaceable by D₂O) 2H ppm.

EXAMPLE 9

Preparation of N²-(benzothiazol-2-yl)-hydrazine carboxylic acid ethyl ester

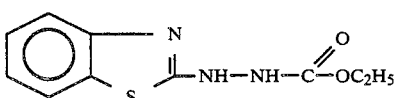

3.4 g (20 mmol) of 2-chlorobenzothiazole are reacted with 2.1 g (20 mmol) of hydrazinocarboxylic acid ethyl ester and 1.4 g (20 mmol) of triethylamine in 10 ml of 99.7% ethanol at reflux temperature for 12 hours. After the reaction solution has been concentrated by evaporation, the residue is taken up in methylene chloride and the organic phase is washed neutral with water and dehydrated over sodium sulphate. After concentration of the organic phase by evaporation, the residue is precipitated with ether.

Colourless crystals, melting point 177°–178° C.
Yield: 0.3 g (6.4% of theoretical)
Rf=0.6 (CH$_2$Cl$_2$/MeOH 9:1)
C$_{10}$H$_{11}$N$_3$O$_2$S (237)

$^1$H-NMR spectrum: (d$_6$-DMSO, TMS as internal standard) δ=1.23 (t) (CH$_3$) 3H, 4.13 (q) (CH$_2$) 2H, 6.93–7.87 (m) (aromatic H)4H, 9.67 (s) (N—H) (replaceable by D$_2$O) 1H, 9.80 (s) (N—H) (replaceable by D$_2$O) 1H ppm.

EXAMPLE 10

Preparation of N$^2$-(benzothiazol-2-yl)-hydrazinocarboxylic acid tert.-butyl ester

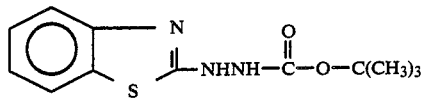

The compound is prepared by a method analogous to that of Example 9 from 6.8 g (40 mmol) of 2-chlorobenzothiazole and 5.3 g (40 mmol) of hydrazinocarboxylic acid tert.-butyl ester.

Colourless crystals, melting point 160°–163° C.
Yield: 0.43 g (4.1% of theoretical)
Rf=0.69 (CH$_2$Cl$_2$/MeOH 95:5)
C$_{12}$H$_{15}$N$_3$O$_2$S (265)

$^1$H-NMR spectrum: (d$_6$-DMSO, TMS as internal standard) δ=1.43 (s) (—C(CH$_3$)$_3$) 9H, 7.00–7.83 (m) (aromatic H) 4H, 9.43 (s) (N—H) (replaceable by D$_2$O) 1H, 9.66 (s) (N—H) (replaceable by D$_2$O) 1H ppm.

We claim:

1. A method of treating a phlogistic condition which comprises administering to a host in need thereof an antiphlogistic effective amount of a benzazole derivative of the formula

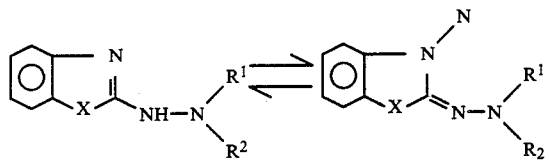

wherein X represents a sulphur or oxygen atom and R$^1$ represents a hydrogen atom and R$^2$ a hydroxymethyl, formyl, lower carbalkoxy or lower acyl group or R$^1$ and R$^2$ together represent the group

wherein R$^3$ and R$^4$ denote, independently of one another, a hydrogen atom or a C$_1$–C$_6$-alkyl group, or a physiologically acceptable salt thereof.

2. The method of claim 1 wherein said antiphlogistic effective amount is 0.05–100 mg/kg.

3. The method of claim 2 wherein said amount is 0.1–10 mg/kg.

4. The method of claim 1 wherein R$^1$ is hydrogen.

5. The method of claim 4 wherein R$^2$ is formyl or carbethoxy.

6. The method of claim 1 wherein R$^1$ and R$^2$ together represent the group

wherein R$^3$ and R$^4$ denote, independently of one another, a hydrogen atom or a C$_1$–C$_6$-alkyl group.

7. The method of claim 6 wherein R$^3$ is hydrogen or methyl and R$^4$ is methyl or ethyl.

8. The method of claim 1 wherein said benzazole derivative is selected from the group consisting of N-(benzothiazol-2-yl)-acetaldehyde hydrazone, N-(benzothiazol-2-yl)-acetone hydrazone, N-(benzothiazol-2-yl)-propionaldehyde hydrazone, N-(benzothiazol-2-yl)-methyl ethyl ketone hydrazone, N-(benzoxazol-2-yl)-acetaldehyde hydrazone, N-(benzoxazol-2-yl)-acetone hydrazone, N-(benzoxazol-2-yl)-propionaldehyde hydrazone, benzothiazol-2-one-(β-formyl hydrazone), N$^2$-(benzothiazol-2-yl)-hydrazine carboxylic acid ethyl ester and N$^2$-(benzothiazol-2-yl)-hydrazinocarboxylic acid tert-butyl ester.

9. A method of inhibiting the lypooxygenase and/or cyclooxygenase route of arachidonic acid metabolism which comprises administering to a host in need thereof an effective inhibitory amount of a benzazole derivative of the formula

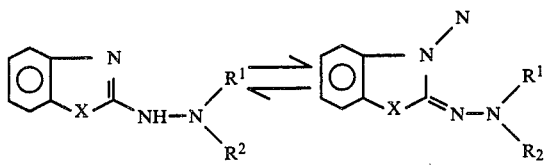

wherein X represents a sulphur or oxygen atom and R$^1$ represents a hydrogen atom and R$^2$ a hydroxymethyl, formyl, lower carbalkoxy or lower acyl group or R$^1$ and R$^2$ together represent the group

wherein R$^3$ and R$^4$ denote, independently of one another, a hydrogen atom or a C$_1$–C$_6$-alkyl group, or a physiologically acceptable salt thereof.

10. The method of claim 9 wherein said amount is 0.05–100 mg/kg.

11. The method of claim 9 wherein said amount is 0.1–10 mg/kg.

12. The method of claim 9 wherein R$^1$ is hydrogen.

13. The method of claim 9 wherein R$^2$ is formyl for carbethoxy.

14. The method of claim 9 wherein R$^1$ and R$^2$ together represent the group

wherein $R^3$ and $R^4$ denote, independently of one another, a hydrogen atom or a $C_1$–$C_6$-alkyl group.

15. The method of claim 9 wherein $R^3$ is hydrogen or methyl and $R^4$ is methyl or ethyl.

16. The method of claim 9 wherein said benzazole derivative is selected from the group consisting of N-(benzothiazol-2-yl)-acetaldehyde hydrazone, N-(benzothiazol-2-yl)-acetone hydrazone, N-(benzothiazol-2-yl)-propionaldehyde hydrazone, N-(benzothiazol-2-yl)-methyl ethyl ketone hydrazone, N-(benzoxazol-2-yl)-acetaldehyde hydrazone, N-(benzoxazol-2-yl)-acetone hydrazone, N-(benzoxazol-2-yl)-propionaldehyde hydrazone, benzothiazol-2-one-(β-formyl hydrazone), $N^2$-(benzothiazol-2-yl)-hydrazine carboxylic acid ethyl ester and $N^2$-(benzothiazol-2-yl)-hydrazinocarboxylic acid tert-butyl ester.

17. A pharmaceutical composition comprising a pharmaceutically acceptable carrier and an antiphlogistic effective amount of a benzazole derivative of the formula

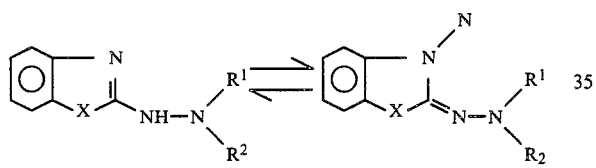

wherein X represents a sulphur or oxygen atom and $R^1$ represents a hydrogen atom and $R^2$ a hydroxymethyl, formyl, lower carbalkoxy or lower acyl group or $R^1$ and $R^2$ together represent the group $$=C<^{R^3}_{R^4}$$

wherein $R^3$ and $R^4$ denote, independently of one another, a hydrogen atom or a $C_1$–$C_6$-alkyl group, or a physiologically acceptable salt thereof.

18. The composition of claim 17 wherein X is sulphur.

19. The composition of claim 17 wherein X is sulphur.

20. The composition of claim 17 wherein $R^1$ is hydrogen and $R^2$ is a hydroxymethyl, formyl, lower carbalkoxy or lower acyl group.

21. The composition of claim 17 wherein $R^2$ is formyl or carbethoxy.

22. The composition of claim 17 wherein $R^1$ and $R^2$ together represent the group $$=C<^{R^3}_{R^4}$$

wherein $R^3$ and $R^4$ denote, independently of one another, a hydrogen atom or a $C_1$–$C_6$-alkyl group.

23. The composition of claim 22 wherein $R^3$ is hydrogen or methyl and $R^4$ is methyl or ethyl.

24. The composition of claim 17 wherein said benzazole derivative is selected from the group consisting of N-(benzothiazol-2-yl)-acetaldehyde hydrazone, N-(benzothiazol-2-yl)-acetone hydrazone, N-(benzothiazol-2-yl)-propionaldehyde hydrazone, N-(benzothiazol-2-yl)-methyl ethyl ketone hydrazone, N-(benzoxazol-2-yl)-acetaldehyde hydrazone, N-(benzoxazol-2-yl)-acetone hydrazone, N-(benzoxazol-2-yl)-propionaldehyde hydrazone, benzothiazol-2-one-(β-formyl hydrazone), $N^2$-(benzothiazol-2-yl)-hydrazine carboxylic acid ethyl ester and $N^2$-(benzothiazol-2-yl)-hydrazinocarboxylic acid tert-butyl ester.

* * * * *